United States Patent
Budidet et al.

(10) Patent No.: US 10,259,778 B2
(45) Date of Patent: Apr. 16, 2019

(54) PROCESS FOR THE PREPARATION OF RALTEGRAVIR

(71) Applicants: Shankar Reddy Budidet, Hyderabad (IN); Jagan Mohan Reddy Sanapureddy, Hyderabad (IN); Subba Reddy Danda, Hyderabad (IN); Bhima Shankar Gangadhara, Hyderabad (IN); Somappa Somannavar Yallappa, Hyderabad (IN); Kishore Karumanchi, Hyderabad (IN); Sivakumaran Meenakshisunderam, Hyderabad (IN)

(72) Inventors: Shankar Reddy Budidet, Hyderabad (IN); Jagan Mohan Reddy Sanapureddy, Hyderabad (IN); Subba Reddy Danda, Hyderabad (IN); Bhima Shankar Gangadhara, Hyderabad (IN); Somappa Somannavar Yallappa, Hyderabad (IN); Kishore Karumanchi, Hyderabad (IN); Sivakumaran Meenakshisunderam, Hyderabad (IN)

(73) Assignee: Aurobindo Pharma Ltd, Hyderabad (IN)

( * ) Notice: Subject to any disclaimer, the term of this patent is extended or adjusted under 35 U.S.C. 154(b) by 32 days.

(21) Appl. No.: 15/525,564

(22) PCT Filed: Nov. 9, 2015

(86) PCT No.: PCT/IB2015/058629
§ 371 (c)(1),
(2) Date: May 9, 2017

(87) PCT Pub. No.: WO2016/075605
PCT Pub. Date: May 19, 2016

(65) Prior Publication Data
US 2017/0334838 A1    Nov. 23, 2017

(30) Foreign Application Priority Data
Nov. 10, 2014    (IN) ............... 5652/CHE/2014

(51) Int. Cl.
| | | |
|---|---|---|
| *C07C 253/30* | (2006.01) | |
| *C07D 273/02* | (2006.01) | |
| *A61K 31/513* | (2006.01) | |
| *A61K 31/506* | (2006.01) | |
| *B01D 11/02* | (2006.01) | |
| *C07D 413/12* | (2006.01) | |
| *C07D 239/54* | (2006.01) | |
| *C07C 269/04* | (2006.01) | |
| *C07C 269/06* | (2006.01) | |
| *C07D 239/557* | (2006.01) | |

(52) U.S. Cl.
CPC .......... *C07C 253/30* (2013.01); *A61K 31/506* (2013.01); *A61K 31/513* (2013.01); *B01D 11/02* (2013.01); *C07C 269/04* (2013.01); *C07C 269/06* (2013.01); *C07D 239/54* (2013.01); *C07D 239/557* (2013.01); *C07D 273/02* (2013.01); *C07D 413/12* (2013.01); *A61K 2300/00* (2013.01)

(58) Field of Classification Search
CPC ... C07C 253/30; C07C 269/04; C07C 269/06; A61K 31/506; A61K 31/513; A61K 2300/00; B01D 11/02; C07D 239/54; C07D 239/557; C07D 273/02; C07D 413/12
USPC ....................................... 558/459
See application file for complete search history.

(56) References Cited

PUBLICATIONS

Humphrey et al., Development of a Second-Generation, Highly Efficient Manufacturing Route for the HIV Integrase Inhibitor Raltegravir Potassium, 2011,Organic Process Research & Development, 15, 73-83 (Year: 2011).*

* cited by examiner

*Primary Examiner* — Kristin A Vajda
(74) *Attorney, Agent, or Firm* — Jay R Akhave

(57) ABSTRACT

The present invention provides a process for the preparation of crystalline anhydrous compound of Formula (X), Further, the present invention relates to the use of compound of Formula (X) preparation of Raltegravir (I) or its pharmaceutically acceptable salt thereof.

Formula X

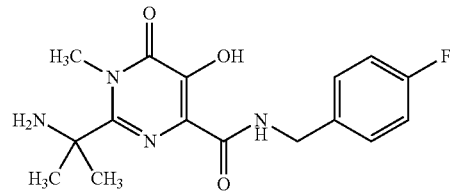

Formula I

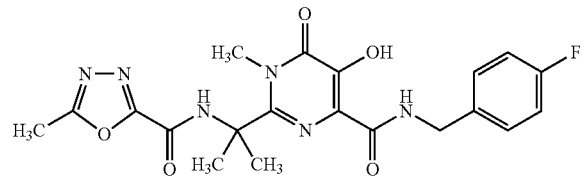

7 Claims, 1 Drawing Sheet

CRYSTALLINE FORM OF 2-(1-AMINO-1-METHYLETHYL)-N-(4-FLUOROBEN-ZYL)-5-HYDROXY-1-METHYL-6-OXO-1,6-DIHYDROPYRIMIDINE-4-CARBOX-AMIDE COMPOUND OF FORMULA (X).
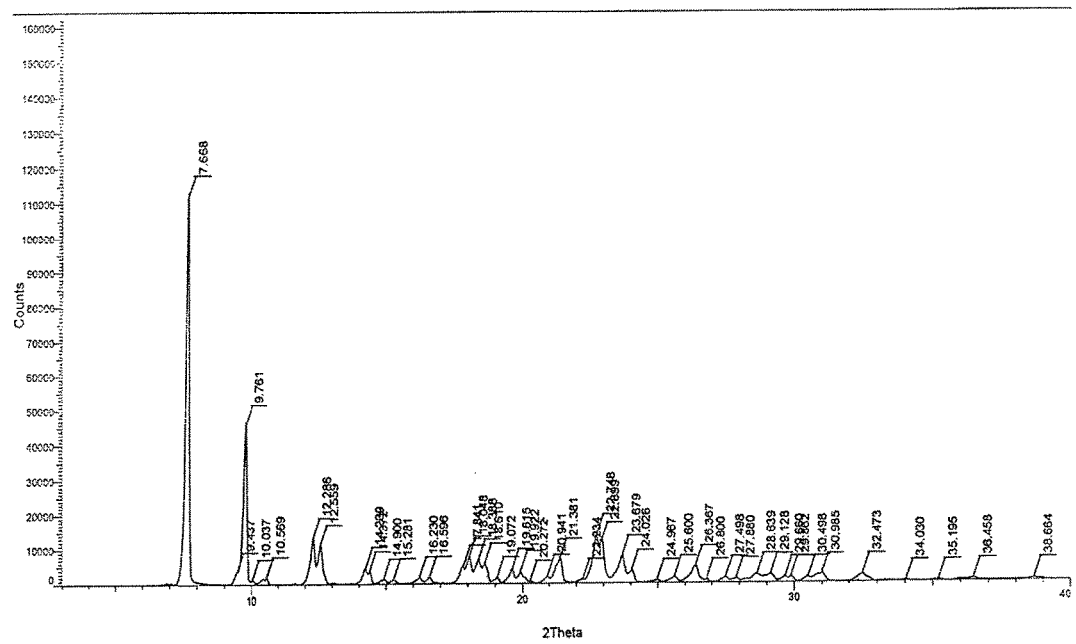

PROCESS FOR THE PREPARATION OF RALTEGRAVIR

FIELD OF THE INVENTION

The present invention relates to an improved process for the preparation of Raltegravir of Formula (I).

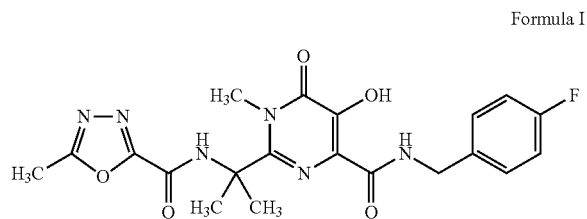 [SMILES: Cc1nnc(C(=O)NC(C)(C)c2nc(C(=O)NCc3ccc(F)cc3)c(O)c(=O)n2C)o1]

Formula I

BACKGROUND OF THE INVENTION

Raltegravir potassium is chemically known as N-[(4-fluorophenyl)methyl]-1,6-dihydro-5-hydroxy-1-methyl-2-[1-methyl-1-[[(5-methyl-1,3,4-oxadiazol-2-yl)carbonyl]amino]ethyl]-6-oxo-4-pyrimidine carboxamide.

Raltegravir is an antiretroviral drug used to treat HIV infection. Raltegravir targets integrase, an HIV enzyme that integrates the viral genetic material into human chromosomes, a critical step in the pathogenesis of HIV. Raltegravir potassium salt is marketed under the trade name Isentress™.

Raltegravir is disclosed in U.S. Pat. No. 7,169,780. U.S. Pat. No. '780 also discloses a process for the preparation of Raltegravir (I) by reacting acetone cyanohydrin (II) with ammonia gas in methanol to produce 2-amino-2-methylpropanenitrile (III), which is further reacted with benzylchloroformate in the presence of sodium carbonate ($Na_2CO_3$) to produce benzyl-1-cyano-1-methylethylcarbamate (IV). Compound (IV) is reacted with hydroxylamine hydrochloride in the presence of KOH in methanol to produce benzyl-2-amino-2-(hydroxyimino)-1,1-dimethylethylcarbamate (V). Compound (V) is reacted with dimethylacetylenedicarboxylate in chloroform to produce methyl-2-(1-{[(benzyloxy) carbonyl]amino}-1-methylethyl)-5,6-dihydroxypyrimidine-4-carboxylate (VI), which is treated with benzoic anhydride in the presence of pyridine to produce methyl-5-(benzoyloxy)-2-(1-{[(benzyloxy)carbonyl]amino}-1-methylethyl)-6-hydroxy-pyrimidine-4-carboxylate (VII), which is further methylated using dimethylsulfate (DMS) in the presence of lithium hydride (LiH) in dioxane to produce methyl-5-(benzoyloxy)-2-(1-{[(benzyloxy)carbonyl] amino}-1-methylethyl)-1-methyl-6-oxo-1,6-dihydroxypyrimidine-4-carboxylate (VIII). Compound (VIII) is reacted with fluorobenzylamine in methanol to produce benzyl-1-(4-{[(4-fluorobenzyl)amino]carbonyl}-5-hydroxy-1-methyl-6-oxo-1,6-dihydropyrimidin-2-yl)-1-methylethylcarbamate (IX), which is hydrogenated in the presence of Pd/C in methanol to produce 2-(1-amino-1-methylethyl)-N-(4-fluorobenzyl)-5-hydroxy-1-methyl-6-oxo-1,6-dihydropyrimidine-4-carboxamide (X). Compound (X) is condensed with 5-methyl-1,3,4-oxadiazole-2-carboxylic acid (XI) in the presence of oxalyl chloride and triethylamine in anhydrous DMF to produce Raltegravir (I).

The process is as shown in Scheme-I below:

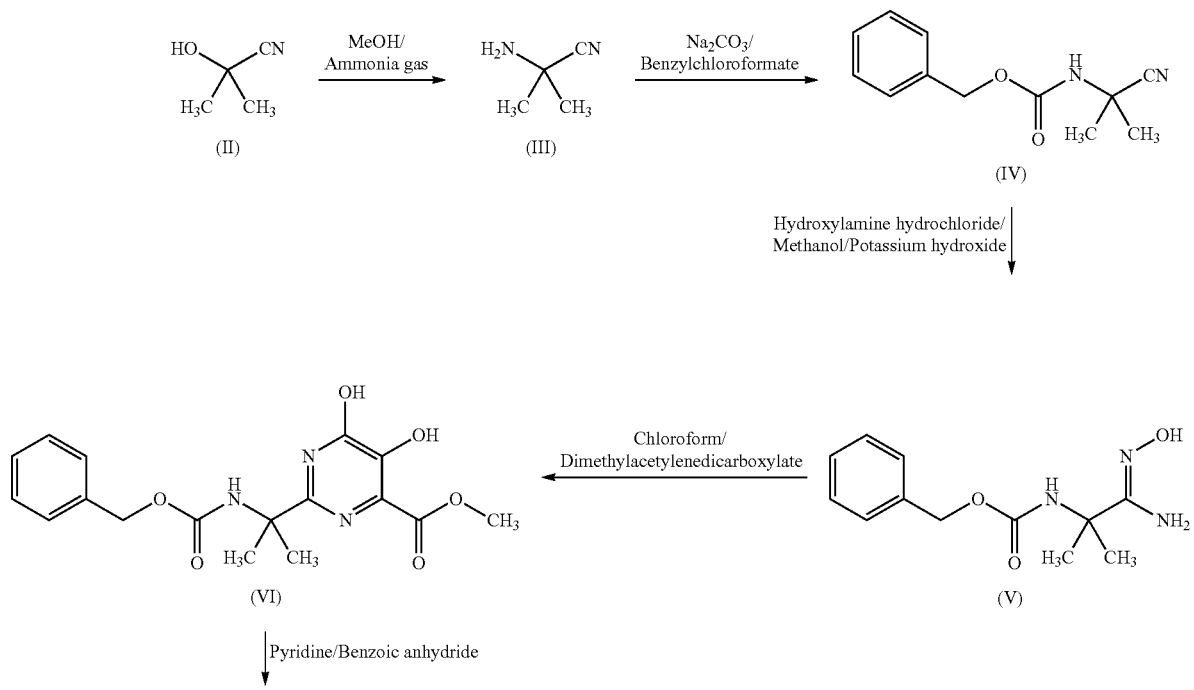

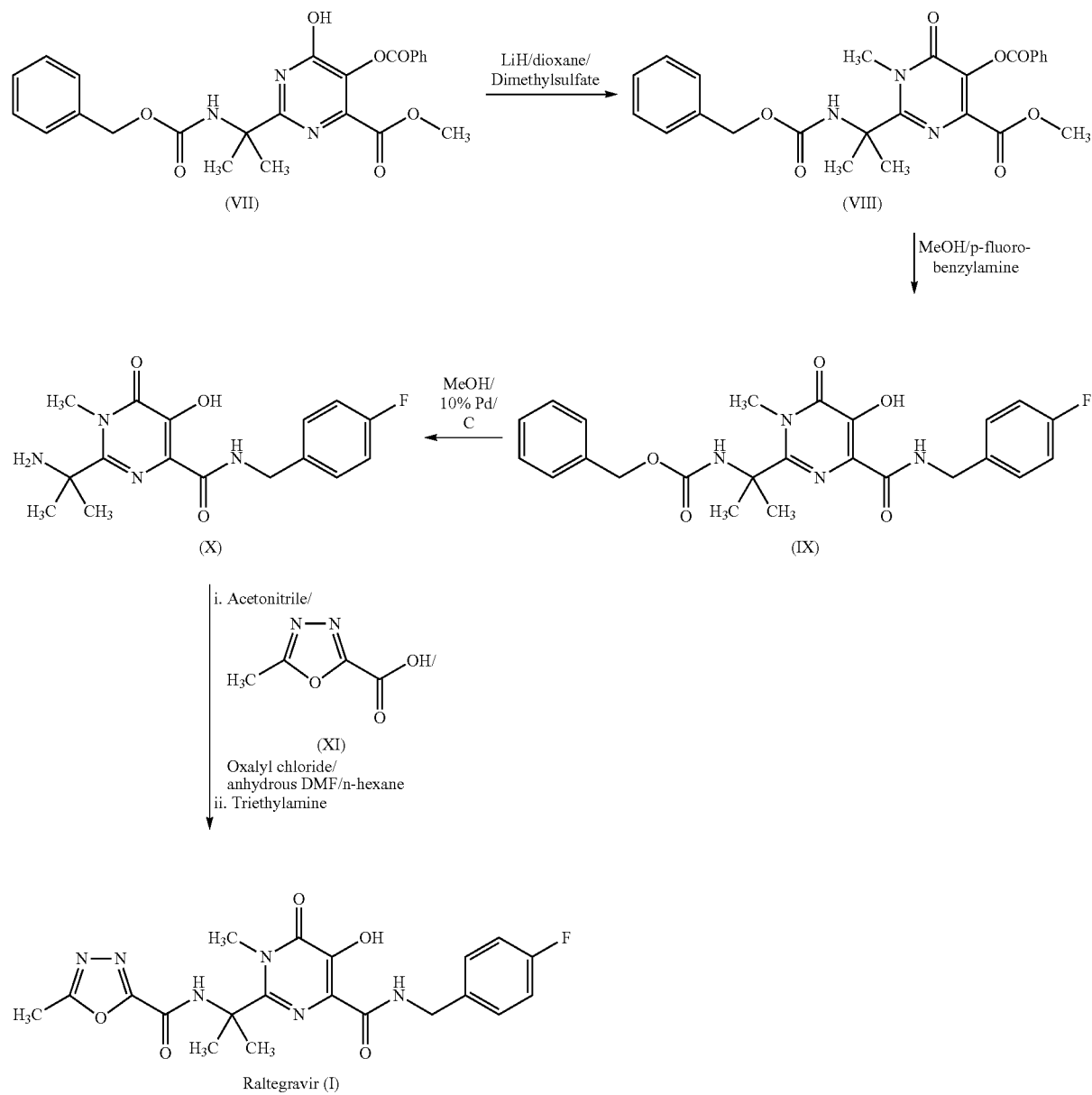
U.S. Pat. No. '780 discloses another variant process for the preparation of Raltegravir (I) by reacting methyl-1,6-dihydro-5-(benzoyloxy)-1-methyl-2-(1-methyl-1-{[5-methyl-1,3,4-oxadiazol-2-yl)-carbonyl]amino}ethyl)-6-oxo-4-pyrimidine carboxylate (XII) with 4-fluorobenzyl amine to produce Raltegravir (I).
The process is as shown in Scheme-II below:
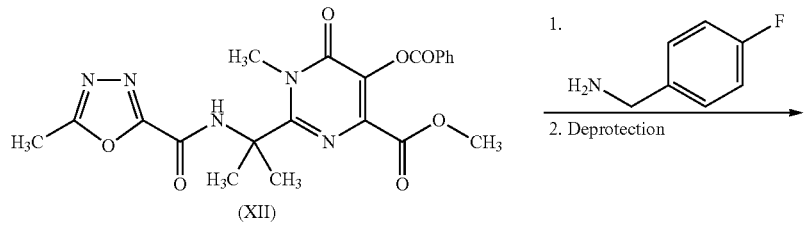

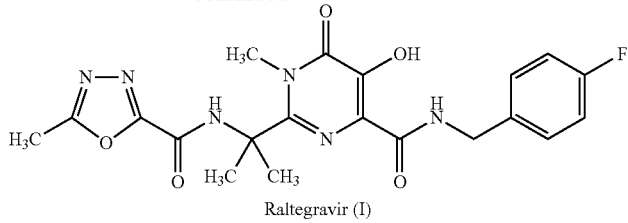

Raltegravir (I)

The major disadvantage with the above processes involves additional protection and de-protection steps for the preparation of Raltegravir. The chemical synthesis which involves more number of steps yields lower yields and the time cycle time of the production is more. This does not make the suitable for commercialization of a chemical process.

U.S. Pat. No. 7,754,731 discloses a process for the preparation of Raltegravir (I) by methylating methyl-2-(1-{[(benzyloxy)carbonyl]amino}-1-methylethyl)-5,6-dihydroxypyrimidine-4-carboxylate (VI) with methyl iodide and magnesium methoxide in dimethylsulfoxide (DMSO) and methanol to produce methyl-5-hydroxy-2-(1-{[(benzyloxy)carbonyl]amino}-1-methylethyl)-1-methyl-6-oxo-1,6-dihydropyrimidine-4-carboxylate (XIII), which is further condensed with p-fluorobenzylamine in ethanol to produce benzyl-1-(4-{[(4-fluorobenzyl)amino]carbonyl}-5-hydroxy-1-methyl-6-oxo-1,6-dihydro-pyrimidin-2-yl)-1-methylethylcarbamate (IX). Compound (IX) is hydrogentaed using Pd/C in the presence of methanesulfonic acid (MSA) in methanol to produce 2-(1-amino-1-methylethyl)-N-(4-fluorobenzyl)-5-hydroxy-1-methyl-6-oxo-1,6-dihydro-pyrimidine-4-carboxamide (X), which is further condensed with 5-methyl-1,3,4-oxadiazole-2-carbonyl chloride (XIa) in the presence of N-methylmorpholine (NMM) in tetrahydrofuran (THF) to produce Raltegravir (I).

The process is as shown in Scheme-III below:

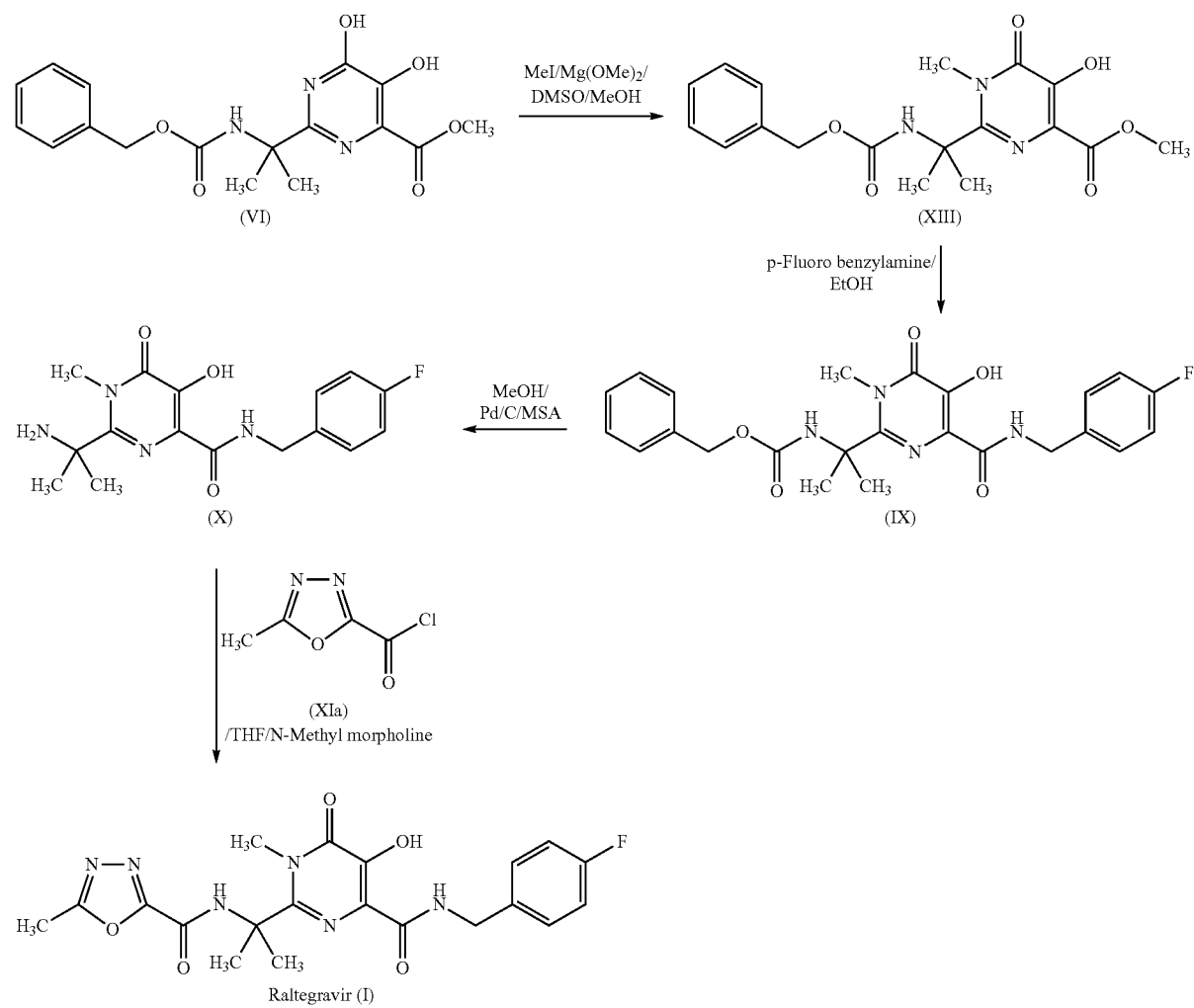

The major disadvantage with the above process is that 2 equivalents acylating agent is used for the completion of acylation step. The acylating agent is more expensive and this process is not suitable for large-scale production of Raltegravir.

U.S. Pat. No. 8,686,141 discloses a process for the preparation of Raltegravir (I) by reacting benzyl-1-(4-{[(4-fluorobenzyl)amino]carbonyl}-5-hydroxy-1-methyl-6-oxo-1,6-dihydro-pyramid-in-2-yl)-1-methylethylcarbamate (IX) with pivaloyl chloride in the presence of triethylamine in ethyl acetate to produce N-[(4-fluorophenyl)methyl]-1,6-dihydro-5-pivaloyloxy-1-methyl-2-[1-methyl-1-[[(phenylmethoxy)carbonyl]amino]ethyl]-6-oxo-4-pyrimidine carboxamide (XIV).

Compound (XIV) is hydrogenated with source of hydrogen in methanol to produce N-[(4-fluorophenyl)methyl]-1,6-dihydro-5-pivalyloxy-1-methyl-2-[1-amino-1-methylethyl]-6-oxo-4-pyrimidinecarboxamide (XV), which is further condensed with 5-methyl-1,3,4-oxadiazole-2-carbonylchloride (XIa) in the presence of NMM in acetonitrile to produce N-[(4-fluorophenyl)methyl]-1,6-dihydro-5-pivalyloxy-1-methyl-2-[1-methyl-1-[[(5-methyl-1,3,4-oxadiazol-2-yl)carbonyl]amino]ethyl]-6-oxo-4-pyrimidinecarboxamide (XVI). Compound (XVI) is hydrolyzed in the presence of aqueous KOH to produce Raltegravir (I).

The process is as shown in Scheme IV below:

However, there is always a need for alternative preparative routes, which for example, use reagents that are less expensive and/or easier to handle, consume smaller amounts of reagents, provide a higher yield of product, involve fewer steps, have smaller and/or more eco-friendly waste products, and/or provide a product of higher purity.

Hence, there is a need to develop cost effective and commercially viable process for the preparation of Raltegravir.

OBJECTIVE OF INVENTION

The main objective of the present invention is to provide a simple and cost effective process for the preparation of Raltegravir (I) with high purity and good yield on a commercial scale.

SUMMARY OF THE INVENTION

The present invention provides a crystalline 2-(1-amino-1-methylethyl)-N-(4-fluoro-benzyl)-5-hydroxy-1-methyl-6-oxo-1,6-dihydropyrimidine-4-carboxamide (X), characterized by X-ray diffraction spectrum which shows peaks at the diffraction angles of about 7.66±0.2, 9.76±0.2, 9.43±0.2; 10.03±0.2, 10.56±0.2, 12.28±0.2, 12.55±0.2, 14.23±0.2, 14.37±0.2, 14.90±0.2, 15.28±0.2, 16.23±0.2, 18.04±0.2, 22.74±0.2, 22.89±0.2 two theta degrees.

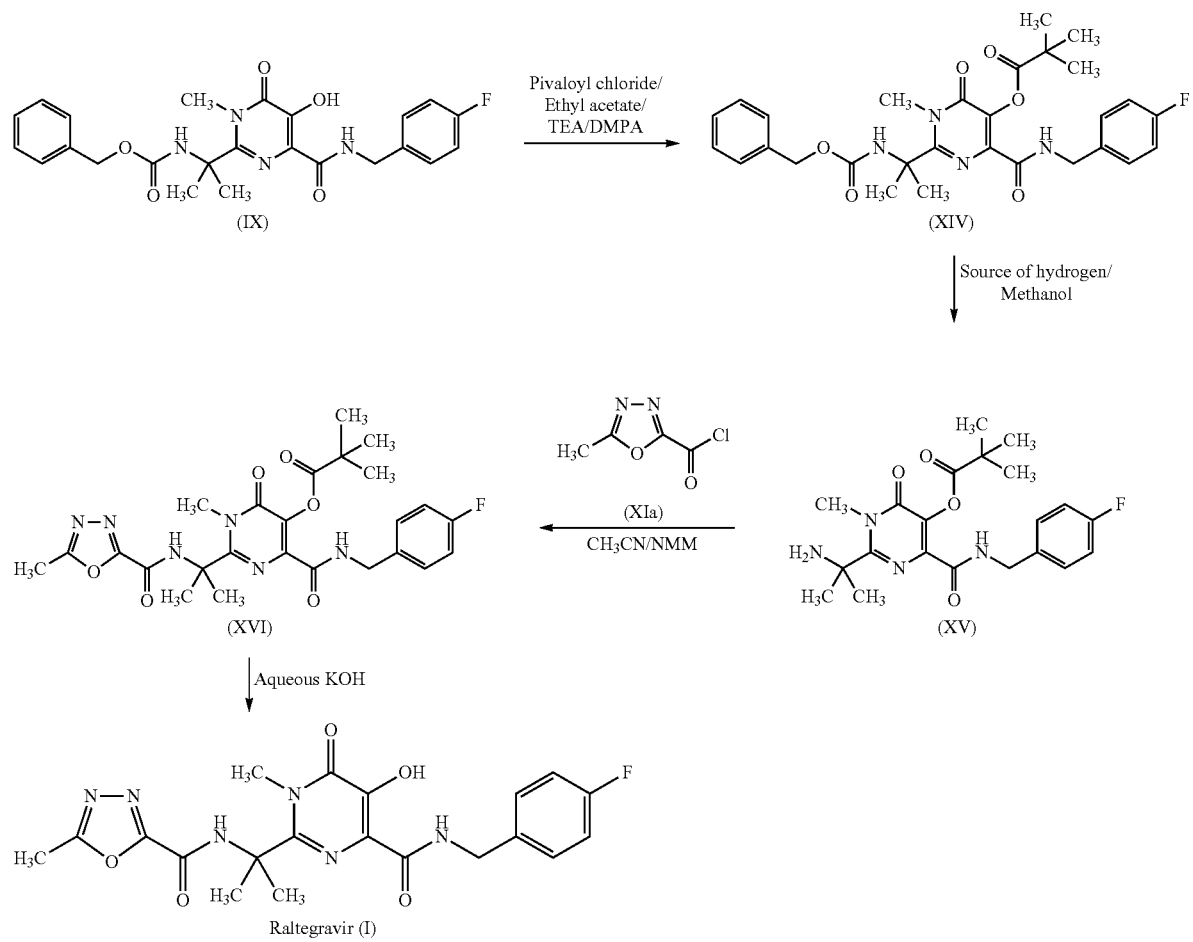

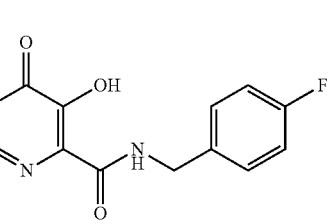
Formula X

In another embodiment, the present invention relates to the use of compound of Formula (X) in the preparation of Raltegravir (I) or its pharmaceutically acceptable salt thereof.

In another embodiment, the present invention provides a process for the preparation of crystalline anhydrous compound of Formula (X),
which comprises:
(i) suspending or dissolving hydrated compound of Formula (X) in a solvents;
(ii) removing the said solvent to isolate crystalline anhydrous compound of Formula (X).

In another embodiment, the present invention provides a process for the preparation of 2-(1-amino-1-methylethyl)-N-(4-fluorobenzyl)-5-hydroxy-1-methyl-6-oxo-1,6-dihydropyrimidine-4-carboxamide Formula (X),
which comprises:
(i) aminating the compound of Formula (II);

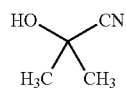
Formula II to produce a compound of Formula (III),

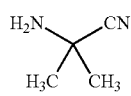
Formula III (ii) reacting the compound of Formula (III) with alkyl chloroformate to produce a compound of Formula (XVII),

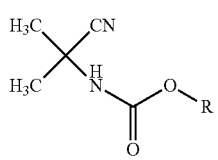
Formula XVII wherein, 'R' represents alkyl group;
(iii) reacting the compound of Formula (XVII) with hydroxylamine or its salt to produce a compound of Formula (XVIII),

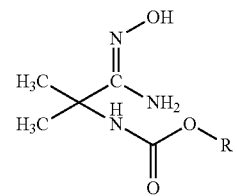
Formula XVIII (iv) reacting the compound of Formula (XVIII) with dimethyl acetylenedicarboxylate (DMADC) to produce a compound of Formula (XIX),

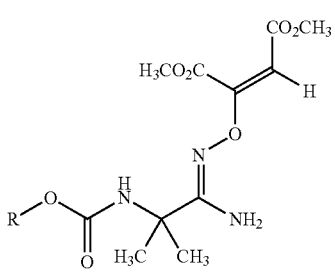
Formula XIX (v) cyclizing the compound of Formula (XIX) to produce a compound of Formula (XX),

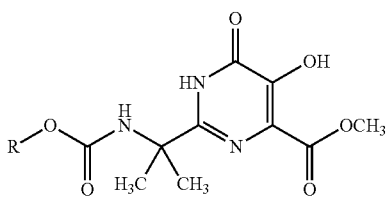
Formula XX (vi) reacting the compound of Formula (XX) with 4-fluorobenzylamine to produce a compound of Formula (XXI),

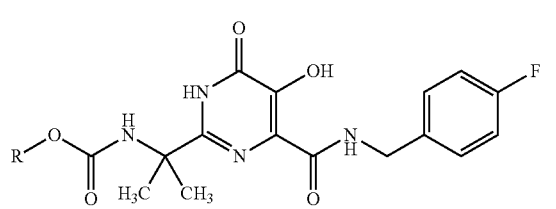
Formula XXI (vii) methylation of the compound of Formula (XXI) to produce a compound of Formula (XXII), Formula XXII

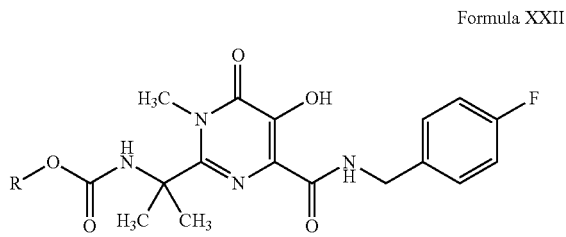

(viii) hydrolysis of the compound of Formula (XXII) to produce a compound of Formula (X).

Formula X

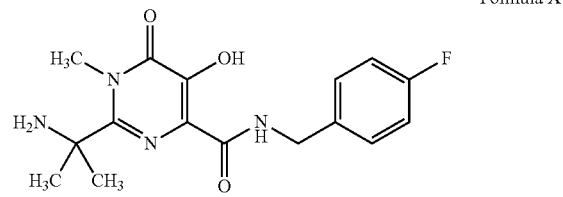

In another embodiment, the present invention provides a process for the preparation of a Raltegravir of Formula I, which comprises:
(i) Protecting the hydroxyl group of compound of Formula (X);

Formula X

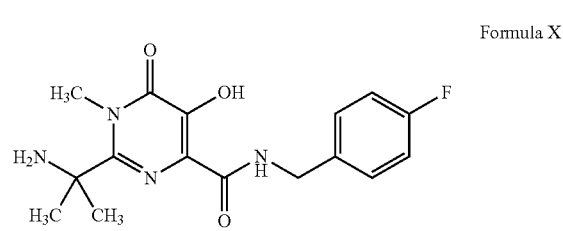 [SMILES: Cn1c(C(C)(C)N)nc(C(=O)NCc2ccc(F)cc2)c(O)c1=O]

to produce a compound of Formula (XXIII),

Formula XXIII

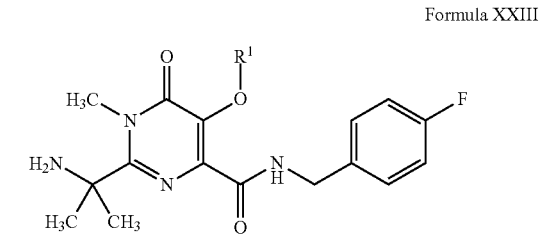

wherein, 'R¹' represents O-protecting group;
(ii) acetylating the compound of Formula (XXIII) with a compound of Formula (XI), Formula XI

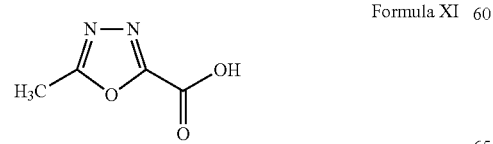

or its reactive derivative, to produce Raltegravir (I).

Formula I

BRIEF DESCRIPTION OF THE DRAWINGS

FIG. 1: illustrates the X-ray powder diffraction pattern of crystalline 2-(1-amino-1-methylethyl)-N-(4-fluorobenzyl)-5-hydroxy-1-methyl-6-oxo-1,6-dihydropyrimidine-4-carboxamide (X).

DETAILED DESCRIPTION OF THE INVENTION

The present invention provides crystalline 2-(1-amino-1-methylethyl)-N-(4-fluoro-benzyl)-5-hydroxy-1-methyl-6-oxo-1,6-dihydropyrimidine-4-carboxamide (X), characterized by X-ray diffraction spectrum which shows peaks at the diffraction angles of about 7.66±0.2, 9.76±0.2, 9.43±0.2, 10.03±0.2, 10.56±0.2, 12.28±0.2, 12.55±0.2, 14.23±0.2, 14.37±0.2, 14.90±0.2, 15.28±0.2, 16.23±0.2, 18.04±0.2, 22.74±0.2, 22.89±0.2 two theta degrees.

In another embodiment, the present invention provides a process for the preparation of crystalline anhydrous compound of Formula (X),
which comprises:
(i) suspending or dissolving hydrated compound of Formula (X) in a solvent or mixture of solvents;
(ii) removing the said solvent to isolate crystalline anhydrous compound of Formula (X).

The solvent used in the step (i) is an aromatic hydrocarbon selected from the group comprising of toluene, o-xylene, p-xylene, m-xylene; aliphatic hydrocarbon selected from the group comprising of hexane, heptane; ketone selected from the group comprising of methyl isobutyl ketone (MIBK); ether selected from the group comprising of n-butyl ether mixture thereof. The reaction is usually allowed to proceed for separation of water by azeotropic distillation at reflux temperature, followed by removal of solvent to isolate the crystalline anhydrous compound of Formula (X).

In another embodiment, the present invention provides a process for the preparation of 2-(1-amino-1-methylethyl)-N-(4-fluorobenzyl)-5-hydroxy-1-methyl-6-oxo-1,6-dihydropyrimidine-4-carboxamide Formula (X),
which comprises:
(i) aminating the compound of Formula (II) to produce a compound of Formula (III);
(ii) reacting the compound of Formula (III) with alkyl chloroformate to produce a compound of Formula (XVII);
(iii) reacting the compound of Formula (XVII) with hydroxylamine or its salt to produce a compound of Formula (XVIII);
(iv) reacting the compound of Formula (XVIII) with dimethyl acetylenedicarboxylate (DMADC) to produce a compound of Formula (XIX);

(v) cyclizing the compound of Formula (XIX) to produce a compound of Formula (XX);
(vi) reacting the compound of Formula (XX) with 4-fluorobenzylamine to produce a compound of Formula (XXI);
(vii) methylation of the compound of Formula (XXI) to produce a compound of Formula (XXII);
(viii) hydrolysis of the compound of Formula (XXII) to produce a 2-(1-amino-1-methylethyl)-N-(4-fluorobenzyl)-5-hydroxy-1-methyl-6-oxo-1,6-dihydropyrimidine-4-carboxamide Formula (X).

Step (i) is carried out in the presence of anhydrous ammonia in a solvent selected from the group comprising of dichloromethane (DCM), tetrahydrofuron (THF), ethyl acetate, acetone, dimethyl formamide (DMF), acetonitrile, dimethyl sulfoxide (DMSO), propylene carbonate or mixture thereof, at a pressure of about 1 psi to about 100 psi and at a temperature about 0° C. to 100° C.

Step (ii) is carried out in the presence of a base. The base is organic base or inorganic base, selected from the group comprising of triethylamine, diisopropylethylamine, 1,8-diazabicyclo[5.4.0]undec-7-ene, 1,4-diazabicyclo-[2.2.2]octane, potassium bicarbonate, potassium carbonate, sodium carbonate, sodium bicarbonate, morpholine derivative, pyridine, dimethylaminopyridine, N-methylmorpholine or mixture thereof, in a solvent selected from the group comprising of dichloromethane, toluene, ethyl acetate, water or mixture thereof.

Step (ii) is carried out at a temperature of about 0° C. to 50° C. After, completion of reaction, the reaction mass is treated with an acid selected from the group comprising of mineral acid or organic acid or mixture thereof. Compound (XVII) is isolated either by conventional methods comprises removal of solvent or by crystallization.

Step (iii) is carried out in the presence or absence of a base is selected from the group comprising of alkali metal hydroxide selected from the group comprising of sodium hydroxide, potassium hydroxide, cesium hydroxide or mixture thereof, in a solvent selected from the group comprising of alcohol selected from the group comprising of C1-C4 aliphatic, straight chain or branched alcohol, water or mixture thereof.

Step (iii) is carried out at a temperature of about 0° C. to 70° C. Further reaction mass is cooled at a temperature of about −5° C. to 25° C., filtered and dried the compound of Formula (XVIII).

Step (iv) is carried out in the presence of a solvent selected from the group comprising of $C_1$-$C_4$ aliphatic alcohol, water or mixture thereof.

Step (iv) is carried out at a temperature of about −30° C. to 10° C. Further reaction mass is cooled at a temperature of about −5° C. to 25° C., filtered and dried the compound of Formula (XIX).

Step (v) is carried out in the presence of a solvent selected from the group comprising of toluene, o-xylene, m-xylene, p-xylene, benzene, pyridine or mixture thereof.

Step (v) is carried out at a temperature of about 50° C. to 150° C. Further reaction mass is cooled at a temperature of about −5° C. to 25° C., filtered and dried the compound of Formula (XX).

Step (vi) is carried out in the presence of a base is selected from organic base selected from the group comprising of triethylamine, diisopropylethylamine, 1,8-diazabicyclo-[5.4.0]undec-7-ene, 1,4-diazabicyclo-[2.2.2]octane; or inorganic base selected from the group comprising of potassium bicarbonate, potassium carbonate, sodium carbonate, sodium bicarbonate, morpholine derivative, pyridine, dimethylaminopyridine, N-methylmorpholine or mixture thereof, in a solvent selected from the group comprising of $C_1$-$C_4$ aliphatic, straight chain or branched alcohol or mixture thereof.

Step-(vi) is carried out at a temperature of about 0° C. to 100° C. After, completion of the reaction, Compound (XXI) is isolated either by conventional method comprises removal of solvent or by crystallization.

Methylation step (vii) is carried out in the presence of a methylating agent selected from the group comprising of methyl halide, dimethyl sulfate, trimethyl silyldiazomethane, dimethyl sulfoxide (DMSO), trimethyl sulfoxonium iodide or mixture thereof. Methyl halide selected from methyl iodide, methyl chloride, methyl bromide, methyl fluoride or mixture thereof and a base is selected from the group comprising of hydride, hydroxide or oxides of metals selected from the group comprising of hydride, carbonate, hydroxide or oxide of magnesium, sodium, potassium and calcium; or magnesium base selected from magnesium oxide (MgO), magnesium hydride ($MgH_2$), magnesium methoxide $Mg(OMe)_2$, magnesium hydroxide ($Mg(OH)_2$), magnesium ethoxide ($Mg(OEt)_2$), magnesium hydroxyl methyl (MgHOMe), magnesium hydroxyl ethyl (MgHOEt) or mixture thereof in a solvent is selected from the group comprising of a polar aprotic solvent or dipolar aprotic solvent selected from dichloromethane (DCM), tetrahydrofuron (THF), ethyl acetate, acetone, dimethyl formamide (DMF), acetonitrile, dimethyl sulfoxide (DMSO), propylene carbonate, N-methyl-2-pyrrolidone, dimethylformamide, dimethylacetamide, dimethyl sulfoxide, water or mixture thereof.

Methylation step is carried out at a temperature of about 50° C. to 150° C. Compound of Formula (XXII) obtained is then isolated from the reaction mixture either directly or by conventional workup and optionally purified by crystallization or precipitation.

Hydrolysis step (viii) is carried out in the presence of a base is selected from the group comprising of alkali metal hydroxide selected from the group comprising of sodium hydroxide, potassium hydroxide, cesium hydroxide or mixture thereof in an alcoholic solvent selected from the group comprising of $C_1$-$C_4$ aliphatic, straight chain or branched alcohol, water or mixture thereof.

Hydrolysis step (viii) is carried out at a temperature of about 20° C. to 120° C. After completion of reaction the reaction mass is treated with an acid selected from the group comprising of hydrochloric acid, in a solvent selected from water and isolated the compound (X) from the reaction mixture.

In another embodiment, the present invention provides a process for the preparation of a Raltegravir of Formula I, which comprises:
(i) protecting the hydroxyl group of compound of Formula (X) to produce a compound of Formula (XXIII);
(ii) acetylating the compound of Formula (XXIII) with a compound of Formula (XI) or its reactive derivative to produce Raltegravir (I).

Step (i) is carried out in the presence of a hydroxyl protecting agent is selected from the group comprising of acetyl chloride, benzoyl chloride, benzyl chloride, trimethyl sillyl chloride, dimethoxytrityl, methoxymethyl ether, p-methoxybenzyl ether, pivaloyl, methylthiomethyl ether, carboxybenzyl (Cbz), tetrahydropyranyl, tetrahydrofuran, trityl, tert-butyldimethylsilyl, tri-iso-propyl-silyloxymethyl, triisopropylsilyl, ethoxyethyl ethers, tertiary butyloxy, allyloxy, methoxymethyloxy, tetrahydropyranyloxy, tertiary-butyldimethylsilyloxy, tertiary-butyldiphenylsilyloxy, acetyloxy, benzoyloxy, and a base selected from the group comprising of triethylamine, diisopropylethylamine, 1,8-diazabicyclo[5.4.0]undec-7-ene, 1,4-diazabicyclo-[2.2.2]octane, potassium bicarbonate, potassium carbonate, sodium carbonate, sodium bicarbonate, morpholine derivative, pyridine, dimethylaminopyridine, N-methylmorpholine or mixture thereof, in a solvent selected from the group comprising of polar aprotic solvent selected from the group comprising of dichloromethane (DCM), tetrahydrofuron (THF), ethyl acetate, acetone, dimethyl formamide (DMF), acetonitrile, dimethyl sulfoxide (DMSO), propylene carbonate or mixture thereof.

Step (i) is carried out at a temperature of about –20° C. to 80° C. After, completion of acetylation reaction, Raltegravir (I) is isolated from reaction mass by conventional methods.

Acetylation step (ii) is carried out in the presence of a base selected from organic base or inorganic base or mixture thereof. Organic base is selected from the group comprising of triethylamine, diisopropylethylamine, 1,8-diazabicyclo[5.4.0]undec-7-ene, 1,4-diazabicyclo-[2.2.2]octane; inorganic base is selected from the group comprising of potassium bicarbonate, potassium carbonate, sodium carbonate, sodium bicarbonate, morpholine derivative, pyridine, dimethylaminopyridine, N-methylmorpholine or mixture thereof in a solvent selected from the group comprising of acetonitrile, methyl acetate, ethyl acetate and propyl acetate, chloroform, dichloromethane or mixture thereof.

Acetylation step is carried out at a temperature of about –20° C. to 50° C. After, completion of acetylation reaction, Raltegravir (I) is isolated from reaction mass by conventional methods.

Raltegravir prepared by any of the above processes is converted to its potassium salt by conventional methods by treating Raltegravir with potassium source and isolated.

The following examples are provided to illustrate the invention and are merely for illustrative purpose only and should not be construed to limit the scope of the invention.

Example-1: Preparation of (Cyano-dimethyl-methyl)carbamic Acid Methyl Ester (XVIIa)

Acetone cyanohydrin (II) (250 g, 2.94 moles) was charged into autoclave at 20-25° C. The autoclave was cooled to 0-5° C. and pressurized to 2-3 Kg/cm$^2$ at 0-30° C. with ammonia gas. The reaction mass was stirred at 20-25° C. till the starting material should be less than 0.5% by GC. After completion of reaction, excess of ammonia gas was degassed by purging nitrogen gas. Reaction mass was diluted with methylene chloride (750 ml) and the resulting reaction mixture was stirred for 10 min and the layer was separated. The aqueous layer was extracted with methylene chloride (125 ml) at 20-25° C. The combined organic layer was concentrated under vacuum at 15-20° C. to about reaction mass contains 475 ml of methylene chloride. The above reaction mass was further diluted with methylene chloride (400 ml) at 20-30° C. and cooled the reaction mass to 10° C. Methyl chloroformate (305.4 g) was added at 10-30° C. in 15 min, diisopropylethylamine (474 g) was added at 10-30° C. for 1 hr and continued stirring at 20-30° C. for 12 hrs. Water (500 ml) was added to the reaction mass and then pH was adjusted to 2-2.2 with conc. hydrochloric acid and stirred for 15 min. The organic layer was washed with water (500 ml). The organic layer was collected and distilled out completely under reduced pressure at 40-45° C. to obtain the title compound (XVIIa) 363 g. The title compound was characterized by $^1$HNMR and mass spectra. Yield: 87%.

Example-2: Preparation of [1-(N-Hydroxycarbamimidoyl)-1-methyl-ethyl] Carbamic Acid Methyl Ester (XVIIIa)

Slurry of hydroxylamine hydrochloride (264.1 g, 3.8 moles) and methanol (720 ml) were cooled to 5° C. Methanolic potassium hydroxide solution [prepared by dissolving potassium hydroxide (246 g) in methanol (900 ml)] was added to the reaction mass in 15 min at 5-10° C. The resultant reaction mixture was stirred for 45 min at 20-30° C. Salt was filtered and washed with methanol (180 ml). Total filtrate was added to above compound (XVIIa) (360 g, 2.54 moles) at 20-25° C. and stirred the reaction mass at 20-25° C. for overnight. Methanol was concentrated under reduced pressure at 40-45° C. and water (180 ml) was added to the concentrated mass and removed traces of methanol under reduced pressure at 40-45° C. 20% w/w Aqueous sodium chloride solution (540 ml) was added to the concentrated reaction mass and stirred for 2 hrs at 20-30° C., further the reaction mass was cooled to 10° C. and stirred for 1 hr at 10-12° C. The product was filtered and washed with cold water (180 ml) and dried at 40-45° C. under reduced pressure to obtain the title compound (XVIIIa) 347 g. The title compound was characterized by $^1$HNMR and mass spectra. Yield: 78%

Example 3: Preparation of 2-(1-Methyloxycarbonylamino-1-methyl-ethyl)-5-hydroxy-6-oxo-1,6-dihydro-pyrimidine-4-caboxylic Acid Methyl Ester (XXa)

A slurry of compound (XVIIIa) (345 g; 1.97 mole) and methanol (1.73 Lt) were cooled to –10° C. Dimethyl acetylene dicarboxylate (308 g, 2.17 mole) was added to above slurry over 40 min at –10 to –8° C. and the resultant reaction mass was stirred for 4 hrs at –10 to –8° C. Methanol was distilled out completely under reduced pressure at 40-45° C. o-xylene (860 ml) was added to the concentrated residue, heated to 125° C. and stirred for 2 hrs at 120-125° C. Further the reaction mass was heated at 135° C. and stirred for 8 hrs at 130-135° C. and then the reaction mass was cooled to 55° C. Methanol (300 ml) was added and stirred for 30 min at 50-55° C. Thereafter the reaction mass was cooled to 35° C., methyl t-butyl ether (1.07 Lt) was added to reaction mixture at 20-35° C. The resultant mixture was stirred for 2 hrs at 20-30° C. The slurry was cooled to 0-2° C. and stirred for 2 hrs at 0-5° C., further slurry was cooled to –10° C. and stirred for 2 hrs at –10 to –5° C. The product was filtered and washed with cold 10% v/v methanol/MTBE (2×690 ml, 0-5° C.) and dried at 40-45° C. under reduced pressure to obtain the title compound (XXa) 337 g. The title compound was characterized by $^1$HNMR and mass spectra. Yield: 60%.

Example 4: Preparation of N-[(4-Fluorophenyl)methyl]-1,6-dihydro-5-hydroxy-2-[(1-methyl-1-[[(methoxy)carbonyl]amino]ethyl-6-oxo-4-pyrimidine Carboxamide (XXIa)

A slurry of compound (XXa) (100 g, 0.35 mole) and methanol (162 ml) were heated to 55° C. Triethylamine (42.52 g, 0.42 mole) was added in one portion to reaction mass at 50-55° C. The reaction mass was heated to 65° C. and 4-fluorobenzylamine (52.7 g, 0.42 mole) was added over 30 min at 65-68° C. The mixture was stirred at reflux temperature for 8 hrs. The reaction mass was cooled to 55° C. and acetic acid (42 g, 0.7 mole) was added over 5 min followed by water (34 ml) was added to reaction mass. The resultant reaction mass was seeded with product (0.1 g) at 55° C. and continued stirring at 55-60° C. for 30 min. Further, water (128 ml) was added to reaction mass over 15 min at 60-62° C. Thereafter the slurry was cooled to 20-25° C. and stirred for 2 hrs at 20-25° C. The product was filtered and washed with 50% v/v aqueous methanol (120 ml) and dried at 40-45° C. to obtain the title compound (XXIa) 128 g. The title compound was characterized by $^1$HNMR and mass spectra. Yield: 96.5%.

Example 4A

A slurry of compound (XXa) (200 g, 0.7 mole) and methanol (320 ml) were heated to 55° C. Triethylamine (77.8 g, 0.769 mole) was added in one portion to reaction mass at 50-55° C. The reaction mass was heated to 60-65° C. and 4-fluorobenzylamine (96.4 g, 0.77 mole) was added over 30 min at 60-65° C. The mixture was stirred at reflux temperature for 8 hrs. The reaction mass was cooled to 55° C. and acetic acid (84 g) was added over 5 min followed by water (68 ml) was added to reaction mass. The resultant reaction mass was seeded with product (0.1 g) at 55° C. and continued stirring at 55-60° C. for 30 min. Further water (260 ml) was added to reaction mass over 15 min at 60-62° C. Thereafter the slurry was cooled to 20-25° C. and stirred for 2 hrs at 20-25° C. The product was filtered and washed with 50% v/v aqueous methanol (2×200 ml) to obtain the title compound (XXIa) (290 g MC: ~11% By KF). Yield: 97.2%, Purity (By HPLC, by area normalization): ~98%

Example 5: Preparation of N-[(4-Fluorophenyl) methyl]-1,6-dihydro-5-hydroxy-1-methyl-2-[(1-methyl-1-[[(methoxy)carbonyl]amino]ethyl]-6-oxo-4-pyrimidine Carboxamide (XXIIa)

A mixture of compound (XXIa) (100 g, 0.264 mole), magnesium hydroxide (30.85 g, 0.53 mole), trimethyl sulfoxonium iodide (116.42 g, 0.53 mole), water (2.9 ml) and N-methyl-2-pyrrolidinone (180 ml) were heated to 100° C. over 1 hr 45 min and maintained at 100° C. for 7 hrs. After completion of the reaction, the reaction mass was cooled to 20° C. and methanol (172 ml) was added. 5N HCl (86.4 ml) was added to reaction mixture over 15 min, followed by seeded with crystal of product (0.1 g) to reaction mass. The mixture was aged for 15 min at 20-25° C. and then a solution of 2.4M aqueous sodium bisulfate (5 ml) was added over 1-2 min. The mixture was aged for 1 hr at 35-38° C. Then 5N HCl (86.4 ml) was added to reaction mass over 40 min. The slurry was gradually cooled to 10° C. and stirred for 1 hr at 10-12° C. The product was filtered and washed with 50% v/v aqueous methanol (2×160 ml) and dried at 45° C. to obtain the title compound (XXIIa) 94 g. The title compound was characterized by $^1$HNMR and mass spectra. Yield: 90.6%

Example 5A

A mixture of compound (XXIa) (145 g, 0.34 mole MC: ~11% by KF), magnesium oxide (29.66 g, 0.736 mole), Trimethyl sulfoxonium iodide (162 g, 0.736 mole) and N-methyl-2-pyrrolidinone (200 ml) were heated to 100° C. in 1 hr 45 min and maintained at 98-100° C. for ~5 h. After completion of reaction, the reaction mass was cooled to 20° C. and methanol (216 ml) was added. 5N HCl (108 ml) was added to reaction mass over 15 min, followed by seeded with crystal of product (0.1 g). The mixture was aged for 15 min at 20-25° C. and then a solution of 2.4M aqueous sodium bisulfate (6 ml) was added over 1-2 min. The mixture was aged for 2 hrs at 31-35° C. 5N HCl (108 ml) was added over 1 h. The slurry was gradually cooled to 10° C. over 1 hr. The product was filtered and washed with 50% v/v aqueous methanol (2×100 ml) and suck dried at 30° C. to obtained the title compound (XXIIa) 125 g, Mc: ~5% by KF. Yield: 88%, Purity (By HPLC, by area normalization): ~98%

Example 6: Preparation of 2-(1-Amino-1-methylethyl)-N-(4-fluorophenyl)methyl]-1,6-dihydro-5-hydroxy-1-methyl-6-oxo-4-pyrimidine Carboxamide Monohydrate (Xa)

To a slurry of compound (XXIIa) (60 g, 0.153 mole) and 2% v/v aqueous n-butanol (180 ml), sodium hydroxide powder (21.42 g, 0.54 mole) was added at 20-25° C.-Exothermic addition. The reaction mass was heated to 110-112° C. and stirred for 2 hrs at 110-112° C. The reaction mass was cooled to 25° C. Water (60 ml) was added to reaction mass and the pH of reaction mass was adjusted to 7-7.5 with con. HCl (30 ml) at 20-30° C. The resultant mass was stirred for 1 hr at 20-25° C. Further the reaction mass was cooled to 0-5° C. and stirred for 1 hr at 0-5° C. The product was filtered and washed with water (130 ml) and dried at 50-55° C. to obtain the title compound (Xa) 39 g. The title compound was characterized by $^1$HNMR and mass spectra. Yield: 72.38%.

Example 6A

To a slurry of compound (XXIIa) (90 g, 0.23 mole) and n-butanol (180 ml), sodium hydroxide powder (35 g, 0.875 mole) was added at 20-25° C.-Exothermic addition. The reaction mass was heated to 100-110° C. and stirred for ~2 hrs at 100-110° C. Further, the reaction mass was cooled to 25° C. Water (270 ml) was added to reaction mass and the pH of the reaction mass was adjusted to 7-7.5 with conc. HCl (95 ml) at 20-30° C. The resultant mass was stirred for 1 hr at 20-25° C. The reaction mass was further cooled to 0-5° C. and stirred for 1 hr at 0-5° C. The product was filtered and washed with water (2×100 ml) and dried at 50-55° C. to obtain the title compound (Xa) 64 g. Yield: 79%, Purity (By HPLC, by area normalization): ~98%

Example 7: Preparation of N-[(4-Fluorophenyl) methyl]-1,6-dihydro-5-hydroxy-1-methyl-2-[1-methyl-1-[[(5-methyl-1,3,4-oxadiazole-2-yl)carbonyl]-aminoethyl]-6-oxo-4-pyrimidine Carboxamide (Raltegravir) (I)

Oxalyl chloride (15.2 g, 0.12 mole) was added to the suspension of oxadiazole-5-methyl-2-carboxylic acid potassium salt (21 g, 0.127 mole) in acetonitrile (100 ml) and N,N-dimethylformamide (1.0 ml) at 0-5° C. and stirred the slurry for 1 hr at 0-5° C. to yield oxadizole-5-methyl-2-carbonylchloride-oxadiazole carbonyl chloride solution (XIa).

Compound (Xa) (20 g, 0.057 mole MC: ~5%) was suspended in toluene (200 ml), azeotropically dried at reflux temperature and the toluene was completely removed by co-distillation with acetonitrile (20 ml). Acetonitrile (80 ml) and N-methylmorpholine (16.5 g, 0.163 mole) were added to the concentrated mass and the resulting slurry was cooled to −5 to 5° C. Oxadiazole-5-methyl-2-carbonylchloride slurry was added to the above slurry at −5 to 5° C. in ~30 min and stirred for 1 hr at 0-5° C. After completion of reaction, acetonitrile was distilled at 50-55° C. under reduced pressure till total volume of reaction mass became to four volume. After that water (80 ml) was added and the pH of the reaction mass was adjusted to ~9.0 with aqueous potassium hydroxide solution. The mass was stirred for 1 hr at 25-30° C. Then the pH of reaction mass was adjusted to 4.0-4.5 with 5N aqueous hydrochloric acid and stirred the mass for 15-min. DM water (120 ml) was added slowly and the resulting slurry was stirred for ~3 hrs at 20-25° C. The product was filtered and washed with mixture of water and acetonitrile (2.5:1.0, 40 ml) and dried at 45-50° C. under reduced pressure to obtain the title compound (I) 20 g. Yield: 79.2%, Purity (By HPLC, by area normalization): ~96%.

Example 7A

Oxalyl chloride (16.2 g, 0.128 mole) was added to the suspension of oxadiazole-5-methyl-2-carboxylic acid potassium salt (21.6 g, 0.13 mole) in methylene chloride (100 ml) and N,N-dimethylformamide (1.0 ml) at 0-5° C. and stirred the slurry for 1 hr at 0-5° C. to yield oxadizole-5-methyl-2-carbonylchloride (XIa).

Compound (Xa) (20 g, 0.0568 mole MC: ~5%) was suspended in toluene (200 ml), azeotropically dried at reflux temperature and the toluene was completely removed under reduced pressure. The reaction mass was cooled to 20-30° C. and methylene chloride (100 ml) was added followed by N-methylmorpholine (16.5 g, 0.163 mole) was added at 20-30° C. Further the resulting slurry was cooled to −5 to 5° C. and the slurry of oxadiazole-5-methyl-2-carbonylchloride was added at −5 to 5° C. in ~30 min and stirred for 1 hr at 0-5° C. After completion of reaction, DM water (100 ml) was added and the pH of the reaction mass was adjusted to ~9.0 with aqueous potassium hydroxide solution. The mass was stirred for 2 hrs at 25-30° C. After that, the pH of reaction mass was adjusted to 4.0-4.5 with 5N aqueous hydrochloric acid and stirred the mixture for 20-min at 25-30° C. The organic layer was separated and washed with aqueous sodium chloride solution (15% w/v, 40 ml) at 25-30° C. The organic layer was separated and distilled off methylene chloride at 35-40° C. under reduced pressure. Methanol (100 ml) was added to the concentrated mass and cooled to 10-15° C. and stirred for 2 hrs. The product was filtered and washed with methanol (40 ml) and dried at 45-50° C. under reduced pressure to obtain the title compound (I) 20 g. Yield: 79.2%, Purity (By HPLC, by area normalization):-96%

Example 8: Preparation of 2-(1-Amino-1-methyl-ethyl)-N-(4-fluorophenyl) methyl]-1,6-dihydro-5-hydroxy-1-methyl-6-oxo-4-pyrimidinecarboxamide Monohydrate (Xa) (with Less Moles of Sodium Hydroxide)

To a slurry of compound (XXIIa) (25 g, 0.0637 mole) and 2% v/v aqueous n-butanol (75 ml), sodium hydroxide powder (6.37 g, 0.159 mole) was added at 20-25° C.-Exothermic addition. The reaction mass was heated to 110-112° C. and stirred for 2 hrs at 110-112° C. The reaction mass was cooled to 25° C. and water (25 ml) was added to reaction mass and the pH was adjusted to 7-7.5 with conc.HCl (12.5 ml) at 20-30° C.

The resultant reaction mass was stirred for 1 hr at 20-25° C., cooled to 0-2° C. and stirred for 1 hr at 0-5° C. The product was filtered and washed with water (50 ml) and dried at 55° C. to obtain the title compound (Xa) 17 g. The title compound was characterized by $^1$HNMR and mass spectra. Yield: 80%

Example 8A

Sodium hydroxide powder (70 g, 1.75 mole) was added to the slurry of compound (XXIIa) (215 g, 0.55 mole) in n-butanol (800 ml) at 25° C. and heated to 110° C. The reaction was maintained for 2 h at 110° C. for complete hydrolysis and concentrated partially distilled under vacuum. Water (600 ml) was added to the reaction mass and pH was adjusted to 7-7.5 with conc. HCl and cooled to 5° C. The slurry was stirred for 2 h, the product was filtered and washed with water (300 ml) to obtain wet product (220 g).

The wet product (55 g) was suspended in toluene (500 ml) and water was separated by azeotropically at reflux temperature, toluene was distilled partially, cooled to 30° C., filtered and dried to obtain the title compound (X) 40 g. Purity (By HPLC, by area normalization): >98%

Example 9: Preparation of N-[(4-Fluorophenyl) methyl}-1,6-dihydro-5-hydroxy-1-methyl-2[1-methyl-1-[[(5-methyl-1,3,4-oxadiazole-2-yl)carbonyl]-amino]ethyl]-6-oxo-4-pyrimidinecarboxamide Potassium Salt (Raltegravir Potassium)(Ia)

Suspended the Raltegravir (I) (300 g, 0.675 mole) in methylene chloride (4.0 lts) at 25-30° C. and the Raltegravir was dissolved at 30-35° C. Carbon enoanticromos (21 g) was added and stirred for 15-20 min at 30-35° C. The carbon enoanticromos was filtered through hyflo and washed with methylene chloride (2×225 ml). Methylene chloride was completely concentrated under atmospheric pressure to get oily mass and ethanol (300 ml) was added at 30-35° C. to the residue mass and distilled out completely ethanol and traces of methylene chloride at 40-45° C. under reduced pressure. Ethanol (3.0 Lt) was added to concentrated mass and heated the slurry to 40-45° C. 35% w/w aqueous potassium hydroxide solution [Prepared, dissolved potassium hydroxide (42.8 g) in water (60.2 g) at 20-40° C.] was added to slurry in 10-15 min. The resultant mixture was stirred for 30 min at 40-45° C. Thereafter the slurry was cooled to 25-30° C. and stirred for 2 hrs 25-30° C. The product filtered, washed with ethanol (2×225 ml) and dried at 40-45° C. to obtain the title compound (Ia) 268 g. The title compound was characterized by $^1$H NMR and mass spectra. Yield: 82.3%.

Example 10: Preparation of N-[(4-Fluorophenyl) methyl]-1,6-dihydro-5-hydroxy-1-methyl-2-[1-methyl-1-[(5-methyl-1,3,4-oxadiazole-2-yl)carbonyl]-amino]ethyl]-6-oxo-4-pyrimidine Carboxamide (Raltegravir)(I)

Oxalyl chloride (68.19 g, 0.537 mole) was added to the suspension of oxadiazole-5-methyl-2-carboxylic acid potassium salt (89.13 g, 0.537) in acetonitrile (270 ml) and N,N-dimethylformamide(2.52 g) at 0-5° C. and stirred the slurry for 2 hrs to yield oxadizole-5-methyl-2-carbonylchloride (XIa).

Compound (X) (90 g, 0.255 mole) was suspended in acetonitrile (1350 ml) and partially distilled out acetonitrile (720 ml) at 80° C. N-methylmorpholine (89.13 g, 0.88 mole) was added to the partially concentrated mass and the resulting slurry was added to the above oxadiazole-5-methyl-2-carbonylchloride slurry at 0-5° C. and stirred for 1 hr at 0-5°

C. The solvent (450 ml) was partially removed under reduced pressure at 40-45° C. and pH of reaction mass was adjusted 5.0-5.8 with acetic acid at 20-25° C. The resulting slurry was stirred for overnight at 20-25° C. Thereafter the reaction mass was cooled to 0-5° C. and stirred for 3 hrs at 0-5° C. The product was filtered and washed with cold water (270 ml) and dried at 45-50° C. under reduced pressure to obtained the title compound Raltegravir (I) 90 g. The title compound was characterized by $^1$HNMR and mass spectra. Yield: 79.2%

Example 11: Preparation of 2-(1-Amino-1-methylethyl)-N-(4-fluorophenyl)-methyl]-1,6-dihydro-5-hydroxy-1-methyl-6-oxo-4-pyrimidine Carboxamide Mono-hydrate (Xa)

Compound (XXII) (2 g, 0.0051 mole) was dissolved in acetic acid (6 ml) at 25-30° C. Aqueous hydrobromic acid (8.6 g, 48% w/w, 0.051 mole)) was added to reaction mass and the reaction mass temperature was raised to 85-90° C. Stirring was continued at 85-90° C. till starting material disappears by TLC, the reaction mass was cooled to 25-30° C. and the pH of the reaction mass was adjusted to 7.0-7.3 with 20% w/v aqueous sodium hydroxide solution. Further the reaction mass was cooled to 0-5° C. and stirred for 2 hrs at 0-5° C. The product was filtered washed with water (5 ml) and dried at 50-55° C. under reduced pressure to obtained the title compound (Xa) 0.7 g. The title compound was characterized by $^1$HNMR and mass spectra. Yield: 38.9%.

Example 12: Preparation of N-[(4-Fluorophenyl) methyl]-1,6-dihydro-5-hydroxy-1-methyl-2-[1-methyl-1-[(5-methyl-1,3,4-oxadiazole-2-yl)carbonyl]-amino]ethyl]-6-oxo-4-pyrimidine Carboxamide (Raltegravir)(I)

Oxalyl chloride (4.76 g, 0.0375 mole) was added to the suspension of oxadiazole-5-methyl-2-carboxylic acid potassium salt (6.48 g, 0.039 mole) in acetonitrile (50 ml) and N,N-dimethylformamide (0.5 ml) at 0-5° C. and stirred the slurry for 1 h at 0-5° C. to yield oxadizole-5-methyl-2-carbonylchloride (XIa).

Compound (Xa) (10.6 g, 0.03 mole, MC: ~5%) was suspended in Toluene (100 ml) and water was separated azeotropically at reflux temperature, toluene was completely distilled and co-distilled with acetonitrile (20 ml). Acetonitrile (50 ml) and N-methylmorpholine (12.14 g, 0.12 mole) were added to the concentrated mass and chlorotrimethylsilane (4.88 g, 0.045 mole) was added to the resulting slurry at 40-55° C., stirred for 60-70 min at 45-55° C. and cooled to −5° C. Oxadiazole-5-methyl-2-carbonylchloride was added to the reaction mass at −5 to 5° C. in 30 min and stirred for 1 h at 0-5° C. to complete the reaction. Reaction mass was partially concentrated under reduced pressure <50° C., water (80 ml) was added and the pH was adjusted to 12.0 with aqueous potassium hydroxide solution at ambient temperature. The reaction mass was stirred for 1 h, acidified with 5N aqueous hydrochloric acid to pH 3.0-3.5 and stirred the slurry for 3 h. The product was filtered, washed with mixture of acetonitrile-water (1.0:2.5, 40 ml) and dried at 50° C. under reduced pressure to obtained the title compound (I) 11 g. Yield: 82.72%; Purity (By HPLC, by area normalization): ~98%

Example 13: Preparation of N-[(4-Fluorophenyl) methyl]-1,6-dihydro-5-hydroxy-1-methyl-2-[1-methyl-1-[(5-methyl-1,3,4-oxadiazole-2-yl)carbonyl]-amino]ethyl]-6-oxo-4-pyrimidine Carboxamide (Raltegravir)(I)

Oxalyl chloride (4.76 g, 0.0375 mole) was added to the suspension of oxadiazole-5-methyl-2-carboxylic acid potassium salt (6.48 g, 0.039 mole) in acetonitrile (50 ml) and N,N-dimethylformamide (0.5 ml) at 0-5° C. and stirred the slurry for 1 h at 0-5° C. to yield oxadizole-5-methyl-2-carbonylchloride (XIa).

Compound (Xa) (10.0 g, 0.028 mole, MC: ~5%) was suspended in toluene (100 ml) and water was separated azeotropically at reflux temperature, toluene was completely distilled and co-distilled with acetonitrile (20 ml). Acetonitrile (50 ml) and N-methylmorpholine (11.33 g, 0.12 mole) were added to the concentrated mass and tert-Butyldimethylsilyl chloride (6.33 g, 0.042 mole) was added to the resulting slurry at 40-55° C., stirred for 60-70 min at 45-55° C. and cooled to −5° C. Oxadiazole-5-methyl-2-carbonylchloride was added to the reaction mass at −5 to 5° C. in 30 min and stirred for 1 h at 0-5° C. to complete the reaction. Reaction mass was partially concentrated under reduced pressure <50° C., water (80 ml) was added and the pH was adjusted to 12.0 with aqueous potassium hydroxide solution at ambient temperature. The reaction mass was stirred for 1 h and acidified with 5N aqueous hydrochloric acid to pH 3.0-3.5 and stirred the slurry for 3 h. The product was filtered and washed with mixture of acetonitrile-water (1.0:2.5, 40 ml). The wet product was stirred in methanol (50 ml), filtered and dried at 50° C. under reduced pressure to obtained the title compound (I) 9.6 g. Yield: 76%, Purity (By HPLC, by area normalization):-98%

Example 14: Preparation of N-[(4-Fluorophenyl) methyl]-1,6-dihydro-5-hydroxy-1-methyl-2-[1-methyl-1-[(5-methyl-1,3,4-oxadiazole-2-yl)carbonyl]-amino]ethyl]-6-oxo-4-pyrimidine Carboxamide (Raltegravir)(I)

Oxalyl chloride (4.76 g, 0.0375 mole) was added to the suspension of oxadiazole-5-methyl-2-carboxylic acid potassium salt (6.48 g, 0.039 mole) in methylene chloride (40 ml) and N,N-dimethylformamide (0.5 ml) at 0-5° C. and stirred the slurry for 1 h at 0-5° C. to yield oxadizole-5-methyl-2-carbonylchloride (XIa).

Compound (Xa) (10.6 g, 0.03 mole, MC: ~5%) was suspended in toluene (100 ml) and water was separated azeotropically at reflux temperature and toluene was completely distilled. Methylene chloride (50 ml) and N-methylmorpholine (12.14 g, 0.12) were added to the concentrated mass. Chlorotrimethylsilane (4.88 g, 0.045 mole) was added to the resulting slurry at 30-40° C., stirred for 2 h at reflux and cooled to −5° C. Oxadiazole-5-methyl-2-carbonylchloride was added to the reaction mass at −5 to 5° C. in 30 min and stirred for 1 h at 0-5° C. to complete the reaction. Reaction mass was washed with DM water (20 ml), 5% w/w potassium hydroxide solution (50 ml) was added and stirred for 1 h 30° C. The reaction mass was acidified with 5N aqueous hydrochloric acid to pH 1.0, stirred for 30 min, organic layer was separated and washed with aqueous sodium chloride solution (30 ml, 15% w/v). The organic layer was concentrated at <40° C. under reduced pressure, stirred with methanol (50 ml), filtered, washed with methanol and dried at 50° C. under reduced pressure to obtained the title compound (I) 10 g. Yield: 75.1%, Purity (By HPLC, by area normalization): ~98%

Example 15: Preparation of N-[(4-Fluorophenyl) methyl]-1,6-dihydro-5-hydroxy-1-methyl-2-[1-methyl-1-[(5-methyl-1,3,4-oxadiazole-2-yl)carbonyl]-amino]ethyl]-6-oxo-4-pyrimidine Carboxamide (Raltegravir)(I)

Oxalyl chloride (4.47 g, 0.0344 mole) was added to the suspension of oxadiazole-5-methyl-2-carboxylic acid potassium salt (5.96 g, 0.0358 mole) in methylene chloride (40 ml) and N,N-dimethylformamide (0.5 ml) at 0-5° C. and stirred the slurry for 1 h at 20-25° C. to yield oxadizole-5-methyl-2-carbonylchloride (XIa).

Compound (Xa) (10.6 g, 0.03 mole, MC: ~5%) was suspended in toluene (100 ml) and water was separated azeotropically at reflux temperature and toluene was completely distilled. Methylene chloride (50 ml) and triethyl amine (12.1 g, 0.12 mole) were added to the concentrated mass. Chlorotrimethylsilane (4.88 g, 0.045 mole) was added to the resulting slurry at ambient temperature, stirred for 2 h and cooled to −5° C. Oxadiazole-5-methyl-2-carbonyl-chloride was added to the reaction mass at −5 to 5° C. in 30 min and stirred for 1 h at 0-5° C. to complete the reaction. Reaction mass was washed with DM water (20 ml), 5% w/w potassium hydroxide solution (50 ml) was added and stirred for 1 h 30° C. The reaction mass was acidified with 5N aqueous hydrochloric acid to pH 1.0, stirred for 30 min, separated organic layer and washed with aqueous sodium chloride solution (30 ml, 15% w/v). The organic layer was concentrated at <40° C. under reduced pressure, stirred with methanol (50 ml), filtered, washed with methanol and dried at 50° C. under reduced pressure to obtained the title compound (I) 11 g. Yield: 82.7%, Purity (By HPLC, by area normalization): ~98%

Example 16: Preparation of N-[(4-Fluorophenyl)methyl]-1,6-dihydro-5-hydroxy-1-methyl-2-[1-methyl-1-[(5-methyl-1,3,4-oxadiazole-2-yl)carbonyl]-amino]ethyl]-6-oxo-4-pyrimidine Carboxamide (Raltegravir)(I)

Oxalyl chloride (4.47 g, 0.0344 mole) was added to the suspension of oxadizole-5-methyl-2-carboxylic acid potassium salt (5.96 g, 0.0358 mole) in methylene chloride (40 ml) and N,N-dimethylformamide (0.5 ml) at 0-5° C. and stirred the slurry for 1 h at 20-25° C. to yield oxadizole-5-methyl-2-carbonylchloride (XIa).

Compound (Xa) (10.6 g, 0.03 mole, MC: ~5%) was suspended in toluene (100 ml) and water was separated azeotropically at reflux temperature and toluene was completely distilled. Methylene chloride (50 ml), N,N-dimethylformamide (10 ml) and Triethylamine (12.1 g, 0.12 mole) were added to the concentrated mass. Chlorotrimethylsilane (4.88 g, 0.045 mole) was added to the resulting slurry at ambient temperature, stirred for 2 h and cooled to −5° C. Oxadiazole-5-methyl-2-carbonylchloride was added to the reaction mass at −5 to 5° C. in 30 min and stirred for 1 h at 0-5° C. to complete the reaction. Reaction mass was washed with DM water (20 ml), added 5% w/w potassium hydroxide solution (50 ml) and stirred for 1 h 30° C. The reaction mass was acidified with 5N aqueous hydrochloric acid to pH 1.0, stirred for 30 min and organic layer was separated and washed with aqueous sodium chloride solution (30 ml, 15% w/v). The organic layer was concentrated at <40° C. under reduced pressure, stirred with methanol (50 ml), filtered, washed with methanol and dried at 50° C. under reduced pressure to obtained the title compound (I) 11 g. Yield: 82.7%, Purity (By HPLC, by area normalization): ~98%.

We claim:
1. A process for the preparation of 2-(1-amino-1-methylethyl)-N-(4-fluorobenzyl)-5-hydroxy-1-methyl-6-oxo-1,6-dihydropyri-midine-4-carboxamide Formula (X), which comprises:

(i) aminating the compound of Formula (II);

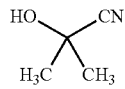

Formula II to produce a compound of Formula (III),)

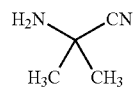

Formula III (ii) reacting the compound of Formula (III) with alkyl chloroformate to produce a compound of Formula (XVII),

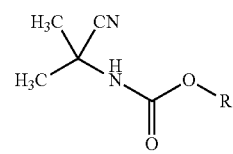

Formula XVII wherein, 'R' represents alkyl group;

(iii) reacting the compound of Formula (XVII) with hydroxylamine or its salt to produce a compound of Formula (XVIII),

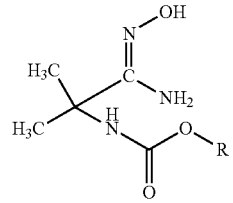

Formula XVIII (iv) reacting the compound of Formula (XVIII) with dimethyl acetylenedicarboxylate (DMADC) to produce a compound of Formula (XIX),

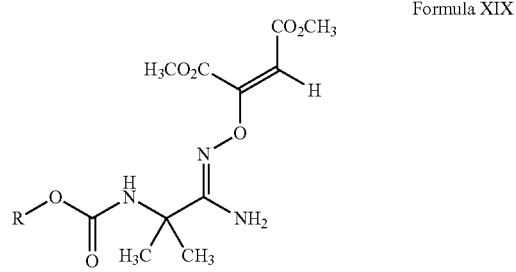

Formula XIX (v) cyclizing the compound of Formula (XIX) to produce a compound of Formula (XX),

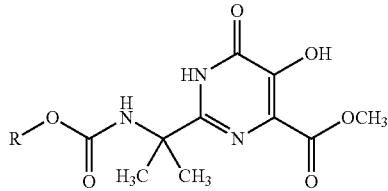

Formula XX (vi) reacting the compound of Formula (XX) with 4-fluorobenzylamine to produce a compound of Formula (XXI),

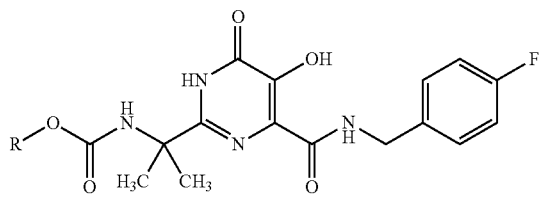

Formula XXI (vii) methylation of the compound of Formula (XXI) to produce a compound of Formula (XXII),

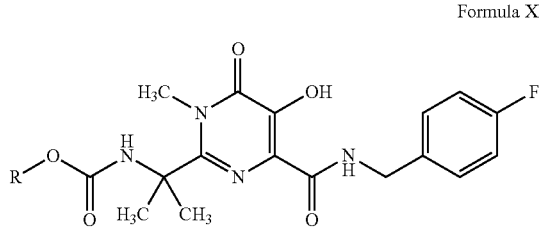

Formula XXII (viii) hydrolysis of the compound of Formula (XXII) to produce a compound of Formula (X).

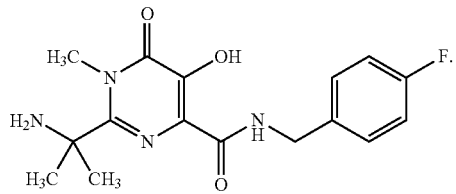

Formula X

2. The process according to claim 1, wherein the amination step (i) is carried out in the presence of ammonia in a solvent selected from the group comprising of dichloromethane (DCM), tetrahydrofuron (THE), ethyl acetate, acetone, dimethyl formamide (DMF), acetonitrile, dimethyl sulfoxide (DMSO), propylene carbonate or mixture thereof.

3. The process according to claim 1, wherein the step (ii) is carried out in the presence of a base selected from the group comprising of organic base or inorganic base, in a solvent selected from the group comprising of dichloromethane, toluene, ethyl acetate, water or mixture thereof.

4. The process according to claim 1, wherein the step (iii) is carried out in the presence of a base selected from the group comprising of alkali metal hydroxide selected from sodium hydroxide, potassium hydroxide, cesium hydroxide or mixture thereof, in a solvent selected from the group comprising of alcohol selected from $C_1$-$C_4$ aliphatic, straight chain or branched alcohol, water or mixture thereof.

5. The process according to claim 1, wherein the Step (iv) and Step (v) is carried out in the presence of a solvent; Step (vi) is carried out in the presence of a base in a solvent; methylation step (vii) is carried out in the presence of a methylating agent and a base in a solvent; hydrolysis step (viii) is carried out in the presence of a base in an alcoholic solvent.

6. The process of claim 1
   which further comprises:
   (i) protecting the hydroxyl group of compound of Formula (X) to produce a compound of Formula (XXIII);
   (ii) acetylating the compound of Formula (XXIII) with a compound of Formula (XI) or its reactive derivative to produce Raltegravir (Formula I).

7. The process according to claim 6, wherein Step (i) is carried out in the presence of a protecting agent and a base in a solvent and acetylation step (ii) is carried out in the presence of a base in a solvent.

\* \* \* \* \*